United States Patent
Alfery

(12) 
(10) Patent No.: US 6,196,224 B1
(45) Date of Patent: Mar. 6, 2001

(54) PERILARYNGEAL ORAL AIRWAY

(76) Inventor: David D. Alfery, 22 Wynstone, Nashville, TN (US) 37215

( * ) Notice: Subject to any disclaimer, the term of this patent is extended or adjusted under 35 U.S.C. 154(b) by 0 days.

(21) Appl. No.: 09/163,978

(22) Filed: Sep. 30, 1998

(51) Int. Cl.$^7$ .................................................. A61M 16/00
(52) U.S. Cl. ................................ 128/207.14; 128/207.15; 128/20.26; 128/201.26; 128/206.29
(58) Field of Search .................. 128/207.15, 207.14, 128/206.29, 200.26, 201.26, DIG. 26; 604/96, 103

(56) References Cited

U.S. PATENT DOCUMENTS

| | | |
|---|---|---|
| D. 261,442 | 10/1981 | Anderson . |
| 3,756,244 | 9/1973 | Kinnear et al. . |
| 3,774,616 | 11/1973 | White et al. . |
| 3,794,026 * | 2/1974 | Jacobs ............................ 128/202.22 |
| 3,908,665 | 9/1975 | Moses . |
| 4,054,135 | 10/1977 | Berman . |
| 4,063,561 | 12/1977 | McKenna . |
| 4,067,331 | 1/1978 | Berman . |
| 4,338,930 | 7/1982 | Williams . |
| 4,446,864 * | 5/1984 | Watson et al. ................... 128/207.14 |
| 4,454,887 | 6/1984 | Krüger . |
| 4,502,482 * | 3/1985 | DeLuccia ........................ 128/207.15 |
| 4,509,514 | 4/1985 | Brain . |
| 4,527,553 * | 7/1985 | Upsher ................................... 128/11 |
| 4,612,927 | 9/1986 | Kruger . |
| 4,683,879 | 8/1987 | Williams . |
| 4,825,858 | 5/1989 | Frankel . |
| 4,827,910 | 5/1989 | Mathews, III . |
| 4,832,020 | 5/1989 | Augustine . |
| 4,848,331 | 7/1989 | Northway-Meyer . |
| 4,852,565 | 8/1989 | Eisele . |
| 4,919,126 | 4/1990 | Baildon . |
| 5,038,766 | 8/1991 | Parker . |
| 5,174,283 | 12/1992 | Parker . |
| 5,203,320 | 4/1993 | Augustine . |
| 5,303,697 | 4/1994 | Brain . |
| 5,323,771 | 6/1994 | Fisher et al. . |
| 5,339,805 | 8/1994 | Parker . |
| 5,443,063 | 8/1995 | Greenberg . |
| 5,477,851 | 12/1995 | Callaghan et al. . |
| 5,653,229 | 8/1997 | Greenberg . |
| 5,720,275 * | 2/1998 | Patil et al. ....................... 128/200.26 |
| 5,743,254 | 4/1998 | Parker . |
| 5,743,258 | 4/1998 | Sato et al. . |
| 5,746,202 * | 5/1998 | Pagan .............................. 128/207.14 |
| 5,771,889 | 6/1998 | Pagan . |
| 5,819,733 | 10/1998 | Bertram . |
| 5,853,004 * | 12/1998 | Goodman ........................ 128/207.15 |
| 5,873,362 * | 2/1999 | Parker ............................. 128/207.14 |
| 5,878,745 | 3/1999 | Brain . |
| 5,896,858 | 4/1999 | Brain . |
| 5,937,860 * | 8/1999 | Cook ............................... 128/207.15 |
| 6,070,581 * | 6/2000 | Augustine et al. ............. 128/207.15 |

FOREIGN PATENT DOCUMENTS

| | | |
|---|---|---|
| 1535060 | 12/1978 | (GB) . |
| WO 92/13587 | 8/1992 | (WO) . |

\* cited by examiner

*Primary Examiner*—John G. Weiss
*Assistant Examiner*—V. Srivastava
(74) *Attorney, Agent, or Firm*—Sughrue, Mion, Zinn, Macpeak & Seas, PLLC

(57) ABSTRACT

An oral airway which is inserted into the pharynx of a patient through the mouth while the patient is undergoing general anesthesia or is undergoing respiratory treatment such as is carried out with cardiopulmonary resuscitation. The oral airway includes a curved hollow, tubular longitudinally extending body member. The body member has a distal end portion for insertion into the patient's mouth and pharynx and a proximal end portion for location at the mouth of the patient. The distal end portion of the body member of the oral airway is extended and shaped so as to be operative to seat deep in the patient's hypo-pharynx and surround the patient's epiglottis and glottis, thereby to hold the patient's soft tissue away from the air channel opening of the patient.

14 Claims, 11 Drawing Sheets

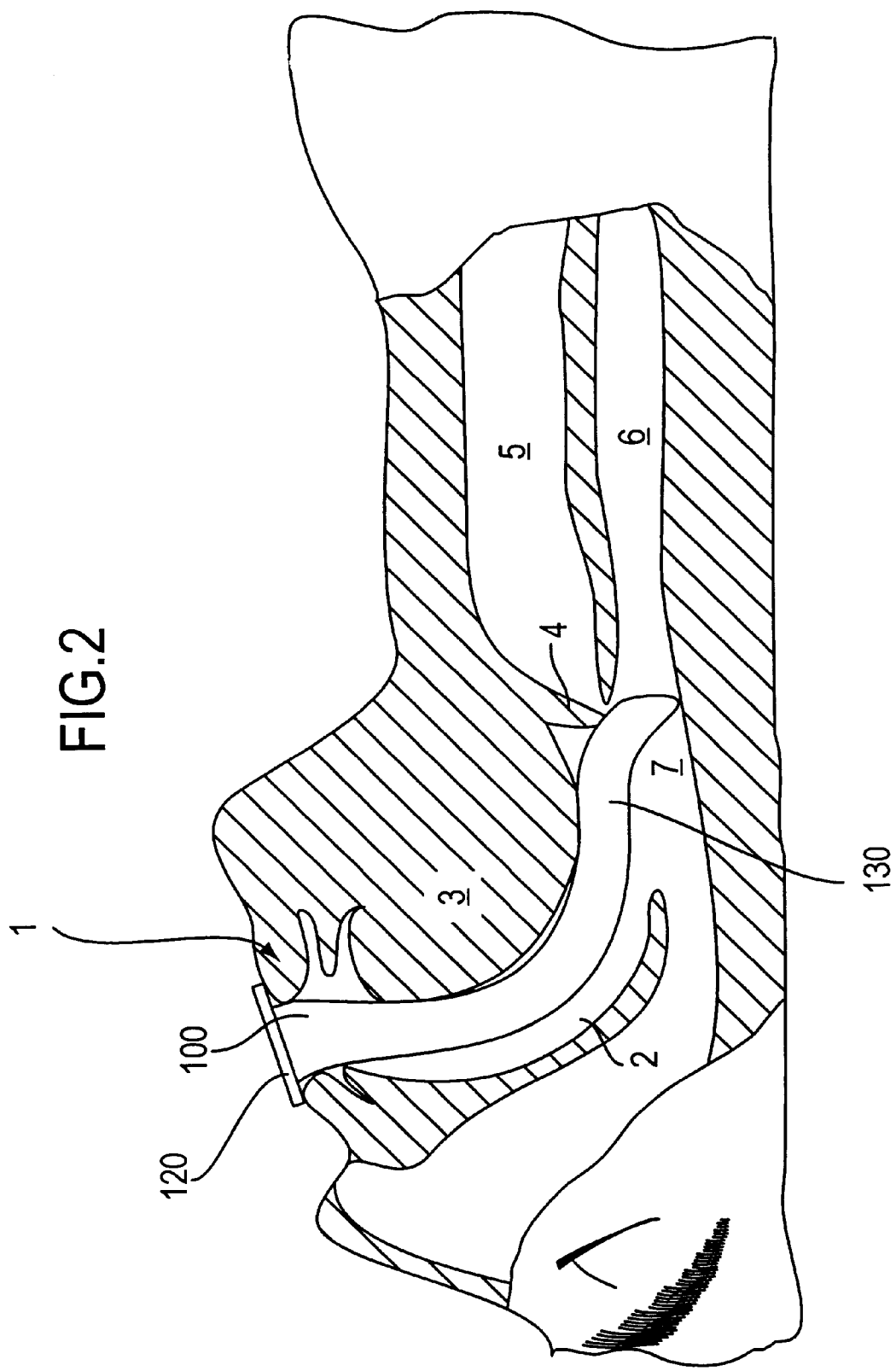

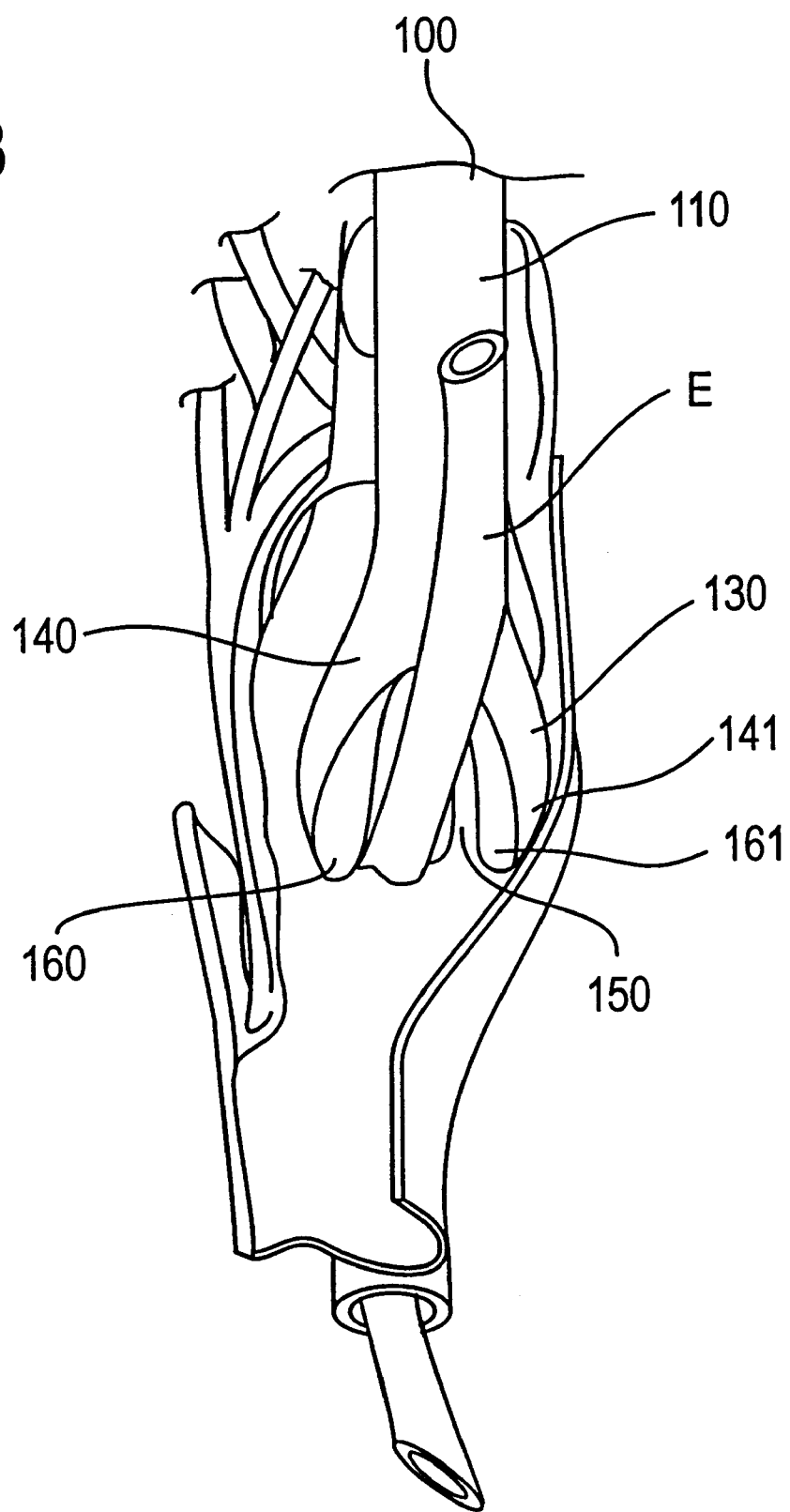

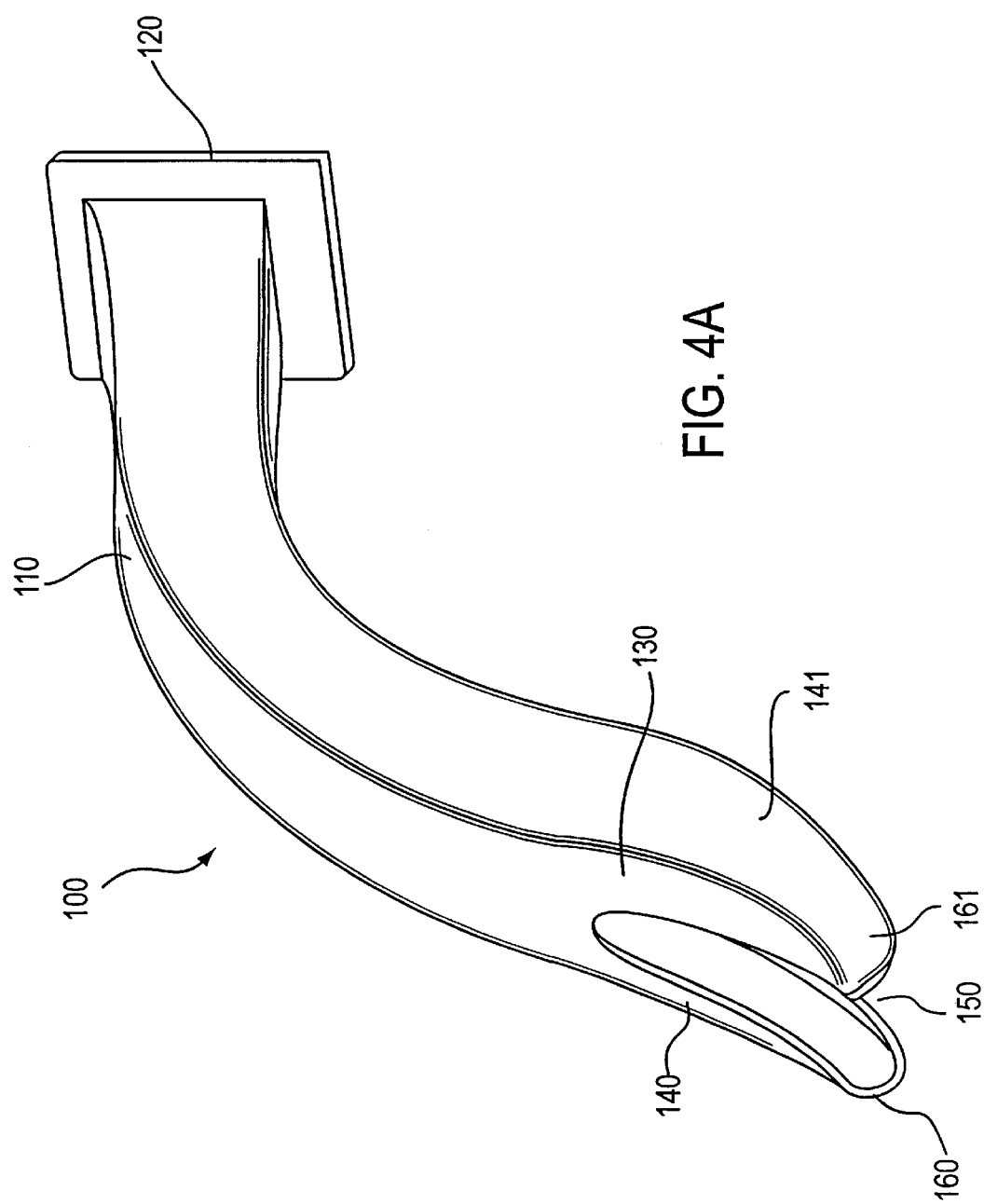

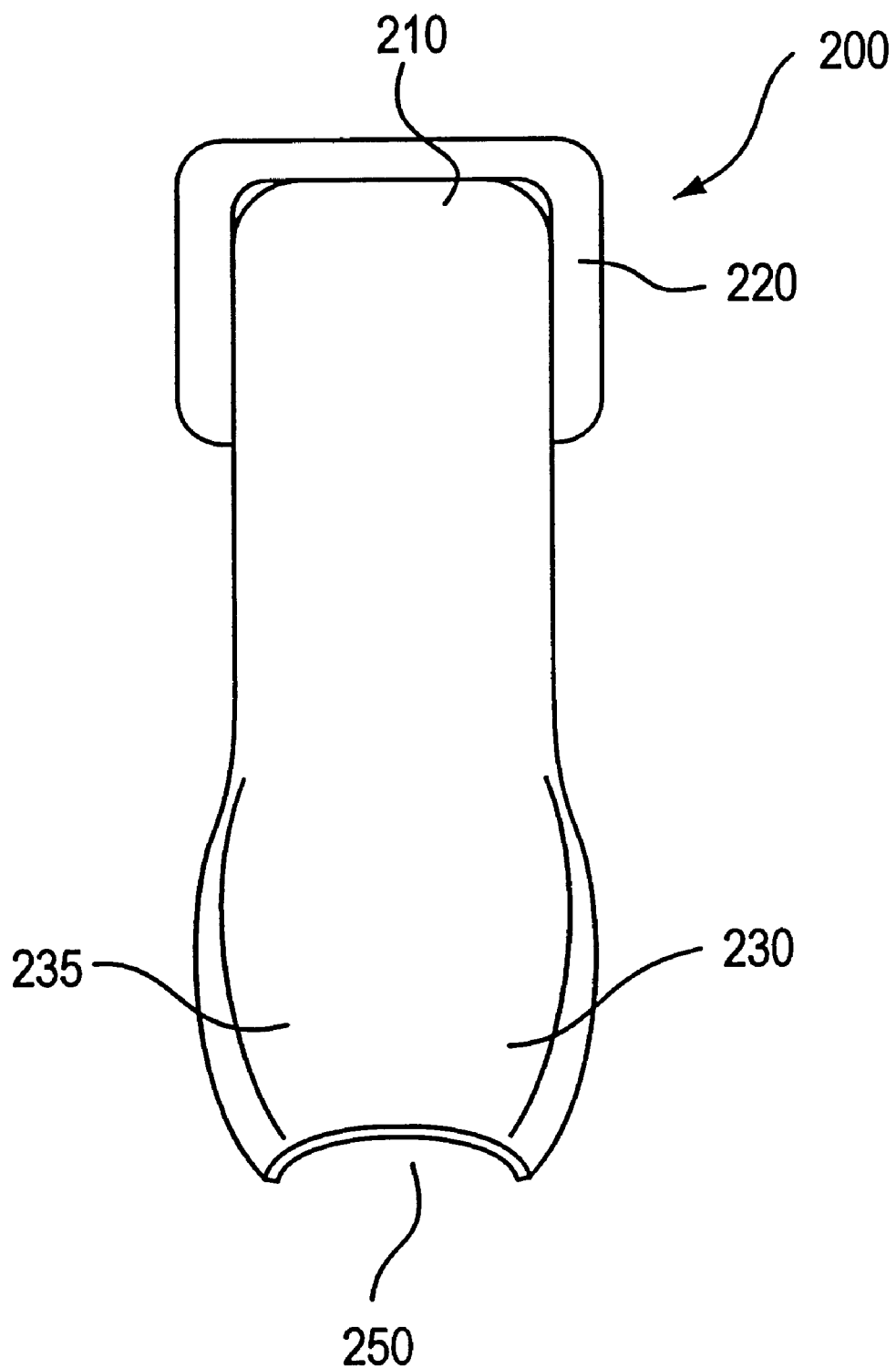

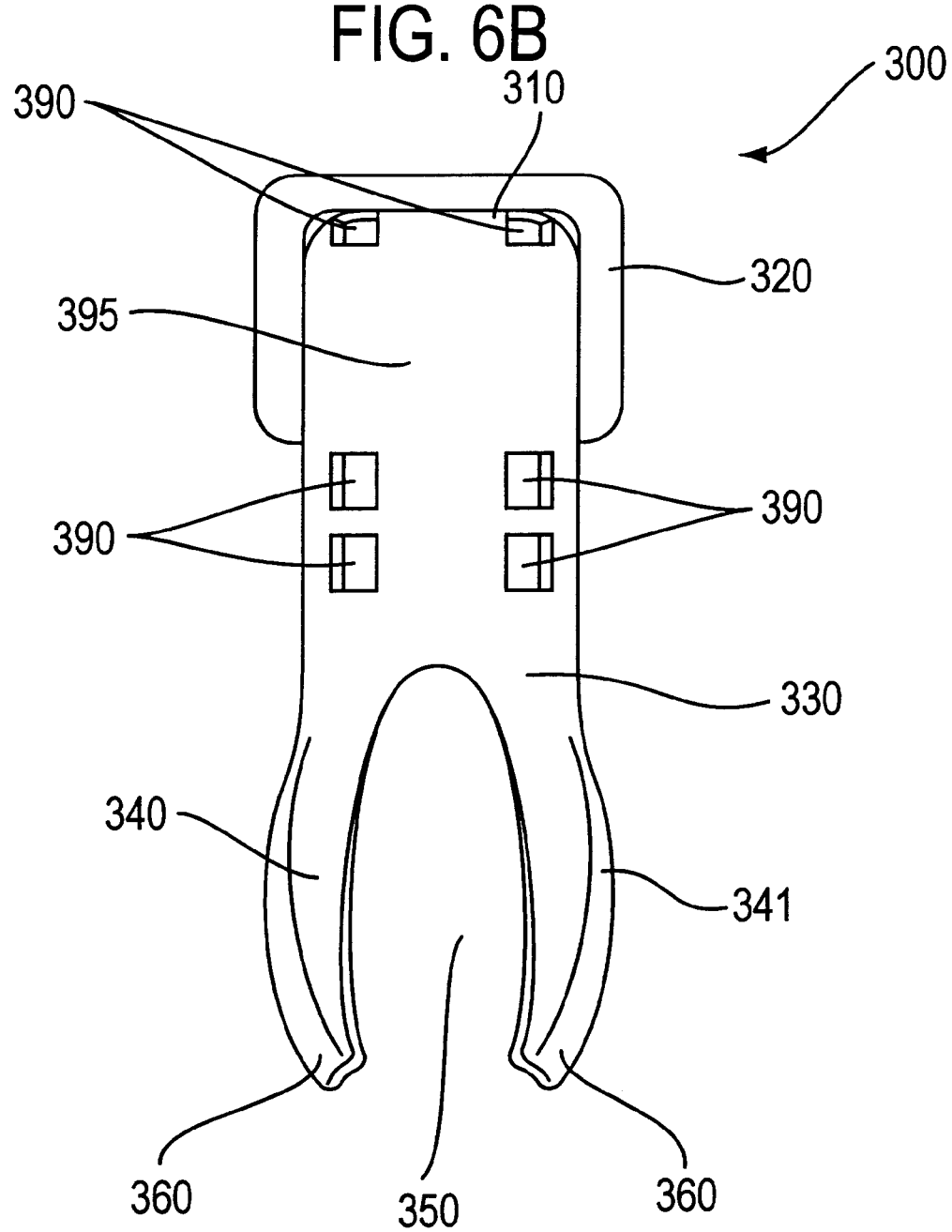

PERILARYNGEAL ORAL AIRWAY

BACKGROUND OF THE INVENTION

1. Field of the Invention

The present invention relates generally to a class of medical devices commonly referred to as oral airways which are inserted through a patient's mouth and into the patient's pharynx while the patient is undergoing general anesthesia or is undergoing respiratory treatment such as is carried out with cardiopulmonary resuscitation. More specifically, the present invention relates to a perilaryngeal oral airway having a distal end portion which is positioned directly around the patient's epiglottis and larynx thereby to maximize the airflow in the vicinity of the glottis and not obstruct airflow into the patient's glottis.

2. Description of the Related Art

Oral airways were introduced into the practice of anesthesia and cardiopulmonary resuscitation several decades ago for two basic purposes. First, they prevent the patient's biting down on and occlusion of a previously placed oral endotracheal tube. Second, and most important, oral airways help to provide a patient airway that allows mask ventilation to be carried out by the practitioner.

For most patients, mask ventilation is carried out successfully by insertion of an oral airway and by a variety of physical adjustments, such as extension of the patient's neck and elevation of the patient's jaw. However, in some patients, no matter what physical adjustments are made or the particular oral airway which is inserted, mask ventilation cannot be successfully achieved. Such cases are literally life-threatening as hypoxemia and death can quickly ensue if the patient's blood is deprived of oxygen due to a lack of ventilation.

When mask ventilation (even with the use of an oral airway) cannot be carried out, there are multiple mechanisms responsible. Most significantly, soft tissue structures in the hypo-pharynx (the area between where conventional oral airways end and the glottis opens into the trachea) collapse inwardly and obstruct airflow. This collapse occurs from both an antero-posterior direction, as well as from the sides of the hypo-pharynx. Unfortunately, all oral airways which have been introduced into practice to date end bluntly well above the epiglottis (the cartilaginous structure just above the glottis or laryngeal opening) and glottis and thus place patients at risk for significant airway obstruction. Other mechanisms of airway obstruction which occur while using oral airways include the patient having large lips covering the outside opening of the oral airway with subsequent inadequate airflow through the nasal passages (due to the solid posterior wall of the airway limiting passage of air into the airway at the level of the nasopharynx).

Additionally, all oral airways are comprised of a hard plastic material throughout their length with no variation in softness between one end of the oral airway and the opposite end. As a result, the distal end (i.e., the end which first enters the mouth and passes down into the pharynx of the patient) often bruises or otherwise damages soft mucosal surfaces of the patient during insertion or once the oral airway has been seated in place.

For example, U.S. Pat. No. 4,919,126 (Baildon) discloses an oral airway formed of plastic which includes an air passageway extending longitudinally through the airway. The distal end has a projecting solid anterior portion which serves as an "epiglottis elevator". As such, the oral airway is blunt-shaped in configuration and ends well above the glottis. For this reason, the Baildon oral airway suffers from the problems discussed above in that it fails to provide any structure to prevent the collapse of soft tissue structures in the hypo-pharynx.

U.S. Pat. Nos. 4,054,135 and 4,067,331 (both to Berman) relate to an intubating pharyngeal airway having a side access for passage of an endotracheal tube. The airway includes a blunt end on the anteriorly extending wall which is designed to fit into the vallecula (area between the epiglottis and tongue). Accordingly, the devices disclosed in both of Berman's patents are similar to the device of Baildon in that they can detrimentally allow soft tissue structures to invaginate inward and thereby occlude the passage of air.

U.S. Pat. No. 3,908,665 (Moses) discloses an oropharyngeal airway wherein the outer diameter of the body portion progressively increases from the end closest to the mouth to the opposite end thereof so as to relieve any obstruction to the flow of air by the base of the tongue falling back on the posterior pharyngeal wall. However, the airway of Moses likewise suffers from the problems discussed in detail above in that the blunt-shaped end terminates well above the glottis, thereby allowing possible soft tissue obstruction to occur.

U.S. Pat. No. 5,203,320 (Augustine) discloses a tracheal intubation guide which similarly seats above the glottis. Moreover, the device of Augustine functions as a guide for placing an endotracheal tube in a "blind" manner and is neither designed for nor could it possibly function to allow mask ventilation to be carried out.

In addition, for some patients it is important to use an airway device which provides a seal within the patient's airway (trachea, oro- or hypopharynx) in order to better allow positive pressure ventilation to be accomplished. Traditionally, this has been achieved by using an endotracheal tube passed between a patient's vocal cords. Recently, in an effort to avoid the deleterious effects of tracheal intubation (e.g., bronchospasm, dental injury, and cardiovascular stimulation), the laryngeal mask airway (LMA) has been introduced into clinical practice. While providing a seal with which to administer positive pressure ventilation, there are several potential problems when using an LMA. First, the device is easily malpositioned so that ventilation is not possible. Second, by directly covering the glottic aperture, trauma to the glottic structures (arrhytenoid cartilages, vocal cords) can occur. In addition, the cost of this product (over $200) becomes a factor when limitations to reuse occur due to physical damage of the device or accidental loss.

Because of the above limitations of the LMA, a cuffed oro-pharyngeal airway has been introduced into clinical practice. U.S. Pat. No. 5,443,063 (Greenberg) describes such a device as an oro-pharyngeal cuff placed over a conventional oral airway. However, this device has several significant limitations which prevent it from functioning adequately. First, the airway suffers from the problems of those previously discussed in that it ends well above the glottis, thereby allowing soft tissue obstruction to impair the flow of oxygen to the lungs. Second, with the cuff placed so far proximally in the oro-pharynx, the device tends to push itself out of the patient's mouth, thereby requiring that the device be secured in place by means of a strap placed around the patient's head. Finally, the cuff is positioned so far proximally in the patient's airway that it often allows leakage of oxygen and anesthetic gases around the cuff, thereby preventing the formation of an air-tight seal. This, of course, makes positive pressure ventilation impossible in those patients.

U.S. Pat. Nos. 3,756,244, 4,612,927, and 4,825,858 are of background interest with respect to the present invention.

SUMMARY OF THE INVENTION

It is an object of the present invention to provide an oral airway wherein the distal end portion thereof is extended and shaped in order to seat deep in the hypo-pharynx and to actually surround the epiglottis and glottis (thus the name "perilaryngeal oral airway"). By extending around the epiglottis and the glottis, the perilaryngeal oral airway of the present invention is able to physically hold the patient's soft tissue in the hypo-pharynx away from the glottic opening.

In particular, the oral airway includes a curved hollow, tubular longitudinally extending body member, the body member having a distal end portion for insertion into the mouth and pharynx of a patient and a proximal end portion for location at the mouth of the patient, wherein the distal end portion of the body member is extended and shaped so as to be operative to seat deep in the patient's hypo-pharynx and terminate just above or surround the patient's epiglottis and glottis, thereby to hold the patient's soft tissue away from the patient's air channel opening.

In one embodiment, the distal end portion of the body member is divided so as to form a pair of elongated extension walls which are operative to seat deep in the patient's hypo-pharynx and surround the patient's epiglottis and glottis, thereby to hold the patient's soft tissue away from the patient's air channel opening. More specifically, a U-shaped or V-shaped opening or notch is formed in the distal end portion as a result of the division or separation of the distal end portion of the body member so as to form the two elongated extension walls and into which the epiglottis and glottis are positioned. The elongated extension walls at the distal end portion expand outward laterally to allow sufficient space in which to accommodate the epiglottis and glottis within the U-shaped or V-shaped opening. The extreme distal ends of the elongated extension walls may be angled inward slightly, thereby providing a smooth contour.

It is a further object of the present invention to form the elongated lateral extension walls to be relatively flexible and soft so that there is at least some "give" as the oral airway is inserted into the patient. The particular firmness of the walls must strike a balance between the need to hold the hypopharyngeal and perilaryngeal structures away from the glottis, the need to move soft tonsillar and oropharyngeal structures to the side as the oral airway is inserted, and the desire for the oral airway to be able to bend inwardly when inserted through the back of the patient's mouth. Likewise, the body member of the oral airway is of sufficient softness and pliability to bend during insertion and to accommodate different angles once successfully inserted into the patient, since a given patient's head and neck may be slightly flexed or extended to provide optimal positioning for mask ventilation. The most proximal end portion of the oral airway is much harder than the distal end portion in order to prevent occlusion by the patient biting down thereon.

In a further embodiment, rather than dividing the distal end portion of the body member so as to form a pair of elongated extension walls, the posterior wall of the distal end portion is filled in. In this way, the posterior wall of the distal end portion serves to better hold tissue away from the larynx. Likewise, the anteriorly placed V or U-shaped opening may be made smaller in order to cover and hold away the epiglottis while still allowing air passage into the glottis.

Further, in either of the above-described embodiments, holes or fenestrations may be formed through the distal anterior wall of the body member of the oral airway in order to provide ventilation should the distal end portion be positioned directly over the glottic opening of the patient, as might occur if the practitioner has selected too large of an oral airway for a particular patient, or the patient has an abnormally high (rostrally) placed glottic opening. Moreover, holes may be formed through the anterior surface of the elongated extension walls and which function to allow ventilation should the oral airway be situated at an abnormal angle such that one of the elongated extension walls covers the glottis. Still further, additional air holes or fenestrations may be formed through the posterior wall of the body member of the oral airway at the region of curvature which is adapted to be positioned at the back of the oropharynx and which allow passage of air through the nasal passages of the patient and into the oral airway per se. Of course, the holes can be dispensed with entirely if desired.

According to a still further embodiment, the oral airway includes an inflatable cuff positioned just above the distally placed notch. Accordingly, the distal end of the perilaryngeal oral airway is easily seated around the larynx, thereby holding the soft tissues away from the glottic aperture, and the more distally positioned cuff is located within the hypopharynx and thereby allows the oral airway to be held in place without external means and avoids the airway leakage which can occur at the base of the tonsillar pillars and soft palate when using the conventional cuffed oro-pharyngeal airway.

In another embodiment of the invention, the cuff may be modified to include the lateral extensions and/or the distal posterior wall of the airway.

The cuff is designed to be inflated with air by means of a pilot tube having a self-sealing proximal valve.

Also contemplated is a method of administering anesthesia or respiratory treatment using an anesthesia or respiratory circuit to a patient using the perilaryngeal oral airway of the present invention.

BRIEF DESCRIPTION OF THE DRAWINGS

Other features and advantages of the present invention will be apparent from the following description taken in connection with the accompanying drawings, wherein:

FIG. 2 is a cross-sectional side view illustrating the use of the perilaryngeal oral airway in accordance with one embodiment of the present invention;

FIG. 3 is a schematic view of the pharynx of a patient wherein the posterior wall has been removed and the interior is viewed from behind, with the distal end portion of one embodiment of the perilaryngeal oral airway according to the present invention being shown seated in position and with an endotracheal tube E in situ;

FIG. 4A is a perspective view showing one embodiment of the perilaryngeal oral airway according to the present invention;

FIG. 5B is a posterior view of the perilaryngeal oral airway of FIG. 5A according to the present invention;

FIG. 6B is a posterior view of the perilaryngeal oral airway of FIG. 6A according to the present invention;

DETAILED DESCRIPTION OF THE PREFERRED EMBODIMENTS

The invention will now be described with reference to the drawings; however, the position of a conventional oral airway is first briefly discussed.

Figure 1:
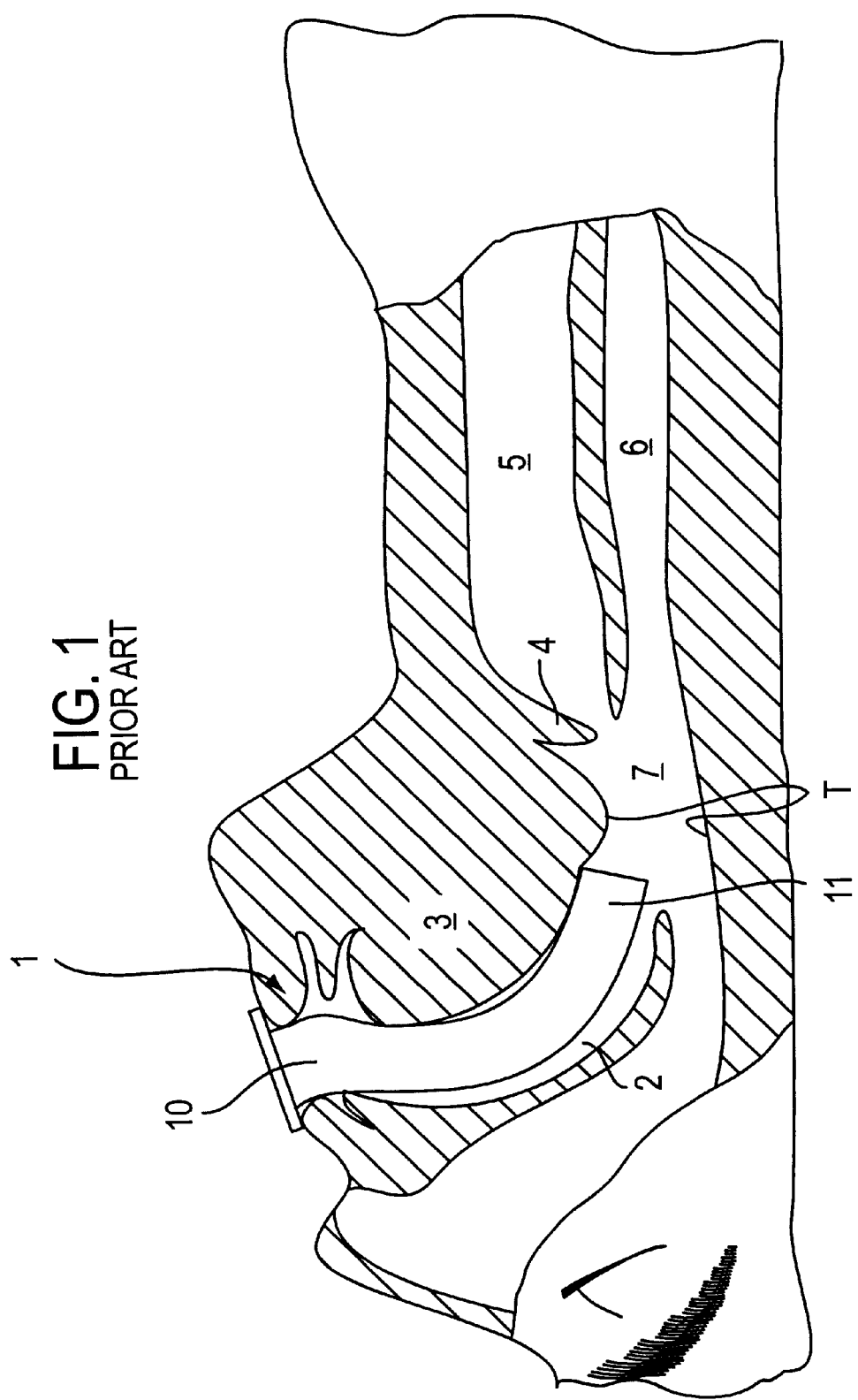
FIG. 1 is a cross-sectional side view illustrating the use of a conventional oral airway inserted in a patient.

FIG. 1 shows a simplified anatomical illustration of a patient's head, including the oral airway defined by the mouth 1, the oral cavity 2, the tongue 3, the epiglottis 4, the trachea 5, the esophagus 6 and the hypopharynx 7. A conventional oral airway 10 is positioned within the patient's oral airway, with the distal end 11 ending well above the glottis so that no structure is provided to prevent the collapse of soft tissue structures T in the hypopharynx.

FIGS. 2, 3, 4A and 4B relate to one embodiment of the perilaryngeal oral airway according to the present invention. Note that in FIG. 2, like elements are denoted with like reference numerals with reference to the patient's oral airway.

Figure 4B:
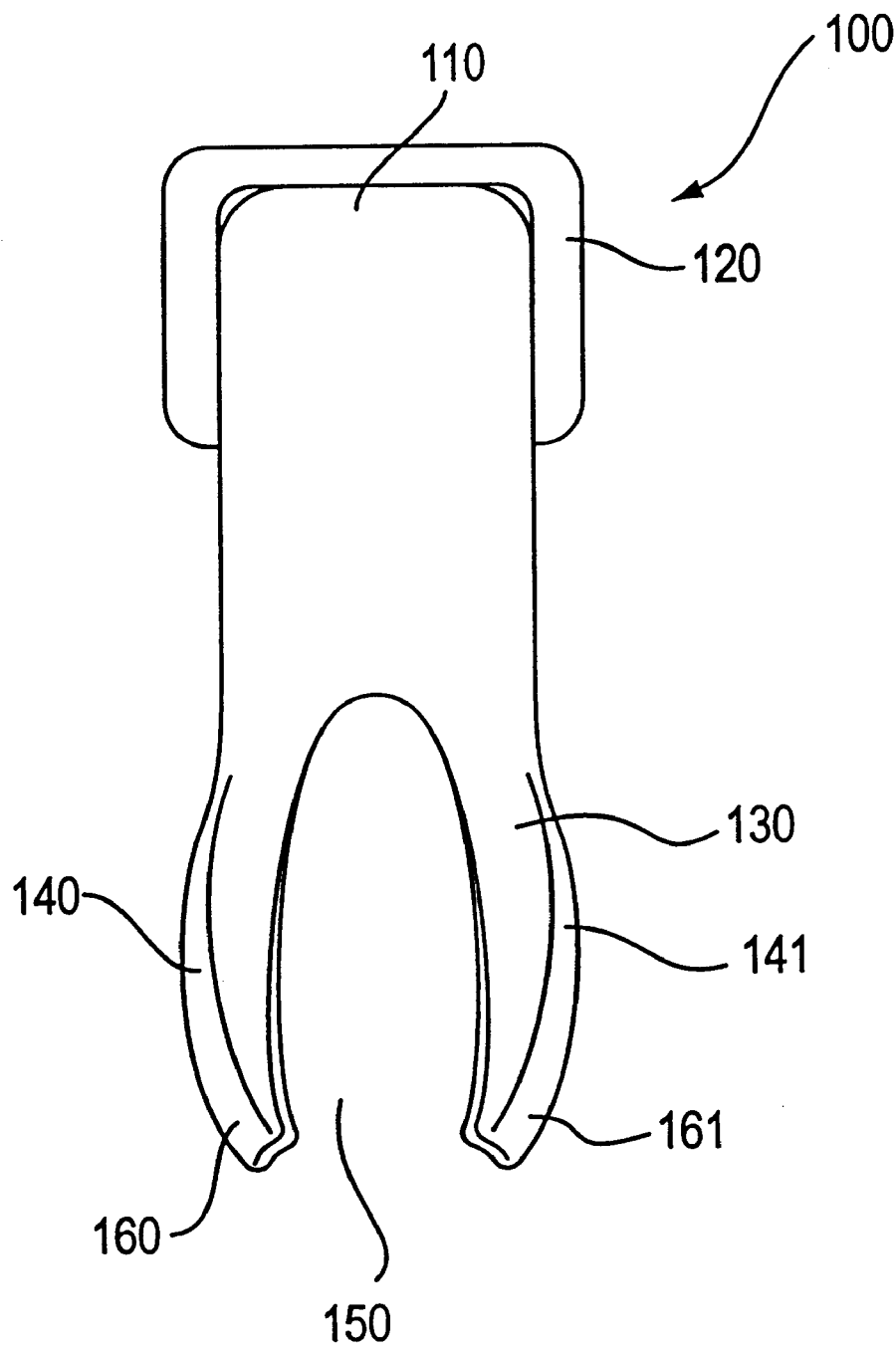
FIG. 4B is a posterior view of the perilaryngeal oral airway of FIG. 4A according to the present invention.

Referring to FIGS. 4A and 4B, the perilaryngeal oral airway 100 includes a curved hollow, tubular longitudinally extending body member 110. The curvature of the body member preferably, but not necessarily, is between 100° and 140°. The body member 110 includes a flanged proximal end portion 120 for location at the mouth of the patient (see FIG. 2). The body member 110 further includes a distal end portion 130 for insertion into the mouth and pharynx of the patient. In the first embodiment, the distal end portion 130 of the body member 110 is divided so as to form a pair of elongated extension walls 140 and 141 which are operative to seat deep in the patient's hypo-pharynx and surround the patient's epiglottis and glottis (see FIGS. 2 and 3), thereby to hold the patient's soft tissue away from the patient's air channel opening.

A U-shaped or V-shaped opening or notch 150 is formed in the distal end portion 130 of the body member 110 so as to form the two elongated extension walls 140 and 141 and into which the epiglottis and glottis are positioned. The elongated extension walls 140 and 141 at the distal end portion preferably, but not necessarily, expand outward laterally to allow for sufficient space in which to accommodate the epiglottis and glottis within the U-shaped or V-shaped opening 150. The extreme distal ends 160 and 161 of the elongated extension walls 140 and 141, respectively, may be angled inwardly slightly, thereby providing a smooth contour. The purpose of the inwardly angled extreme distal ends is to allow the ends to be safely inserted past the tonsillar pillars at the back of the patient's mouth. By forming the inwardly-shaped surface, the slightly narrower most distal end can push up against very large tonsils and move them laterally to the sides as the perilaryngeal oral airway is inserted.

The elongated lateral extension walls 140 and 141 are preferably, but not necessarily, formed to be relatively flexible and soft so that there is at least some "give" as the perilaryngeal oral airway is inserted into the patient. The particular firmness of the walls must strike a balance between the need to hold the hypo-pharyngeal and perilaryngeal structures away from the glottis, the need to move the soft tonsillar and oropharyngeal structures to the side as the oral airway is inserted, and the desire for the oral airway to be able to bend inwardly when inserted through the back of the patient's mouth. Likewise, the body member 110 of the perilaryngeal oral airway 100 is preferably, but not necessarily, of sufficient softness and pliability to bend during insertion and to accommodate different angles once it is successfully inserted into the patient, since a given patient's head and neck may be slightly flexed or extended to provide optimal positioning for mask ventilation. The most proximal end portion 120 of the oral airway is much harder than the distal end portion 130 in order to prevent occlusion by the patient biting down thereon.

Figure 5A:
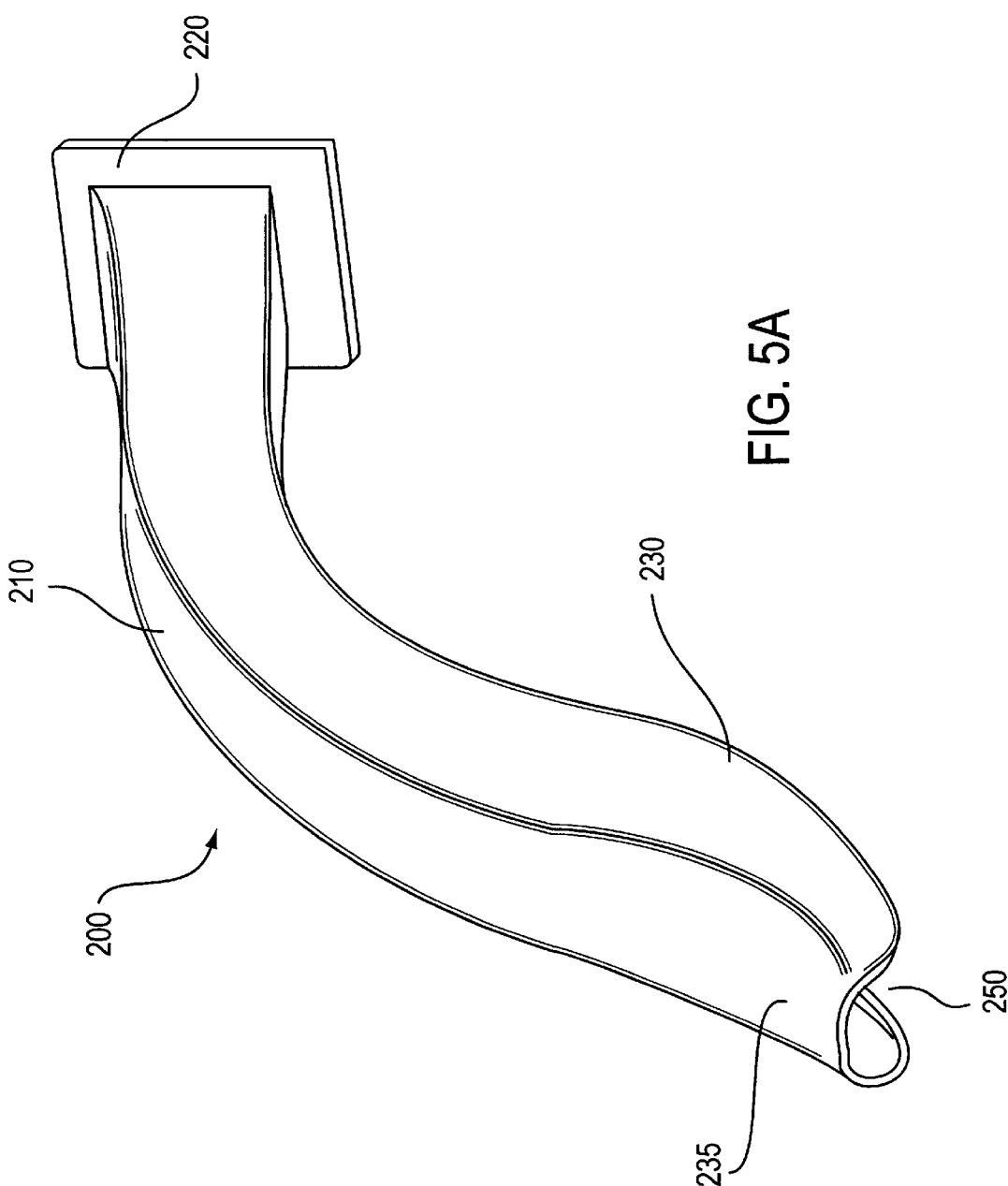
FIG. 5A is a perspective view showing a further embodiment of the perilaryngeal oral airway according to the present invention.

FIGS. 5A and 5B show a further embodiment of the perilaryngeal oral airway according to the present invention wherein the distal end portion 230 is modified in comparison to the oral airway of the previous embodiment. Note that like elements are denoted with like reference numerals, but preceded by the reference numeral "2". In particular, in this embodiment, the distal end portion 230 has a "filled-in" distal posterior wall 235 in order to better hold tissue away from the larynx. The anterior wall includes a notched portion 250 as in the previous embodiment. The body member 210 of the oral airway preferably, but not necessarily, is of sufficient softness and pliability to bend during insertion and to accommodate different angles once successfully inserted into the patient.

Figure 6A:
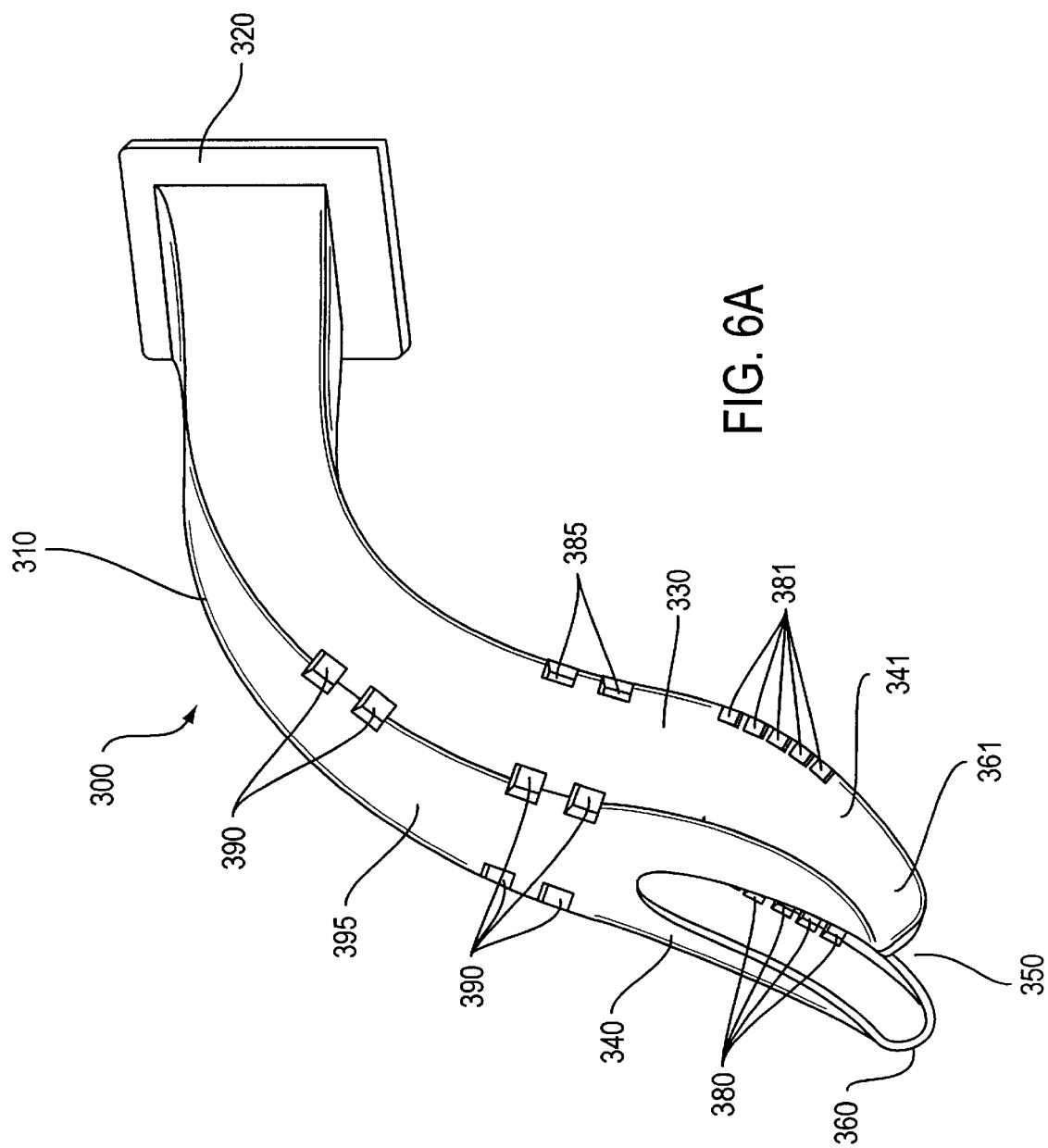
FIG. 6A illustrates the use of holes or fenestrations in one of the embodiments of the perilaryngeal oral airway according to the present invention.

FIGS. 6A and 6B illustrate a still further embodiment of the perilaryngeal oral airway according to the present invention. Again, like elements are denoted with like reference numerals, but preceded by the number "3". In particular, holes or fenestrations 385 may be formed through the distal anterior wall of the body member 310 of the oral airway in order to provide ventilation should the distal end portion 330 be positioned directly over the glottic opening of the patient, as might occur if the practitioner has selected too large of an oral airway for a particular patient, or where the patient has an abnormally high (rostrally) placed glottic opening.

Moreover, holes 380 and 381 may be formed through the anterior surface of the elongated extension walls 340 and 341, respectively, and which function to allow ventilation should the oral airway be situated at an abnormal angle such that one of the elongated extension walls covers the glottis.

Still further, additional air holes or fenestrations 390 may be formed through the posterior wall 395 of the body member 310 of the oral airway at the region of curvature which is adapted to be positioned at the back of the oropharynx and which allow passage of air through the nasal passages of the patient and into the oral airway per se.

Of course, while the holes and fenestrations are shown in connection with the first embodiment of the present invention which includes the elongated extension walls 340 and 341, the holes or fenestrations may likewise be used with the second embodiment which includes the filled-in distal posterior wall. Of course, the holes can be dispensed with entirely in both the first and second embodiments if desired.

Figure 7:
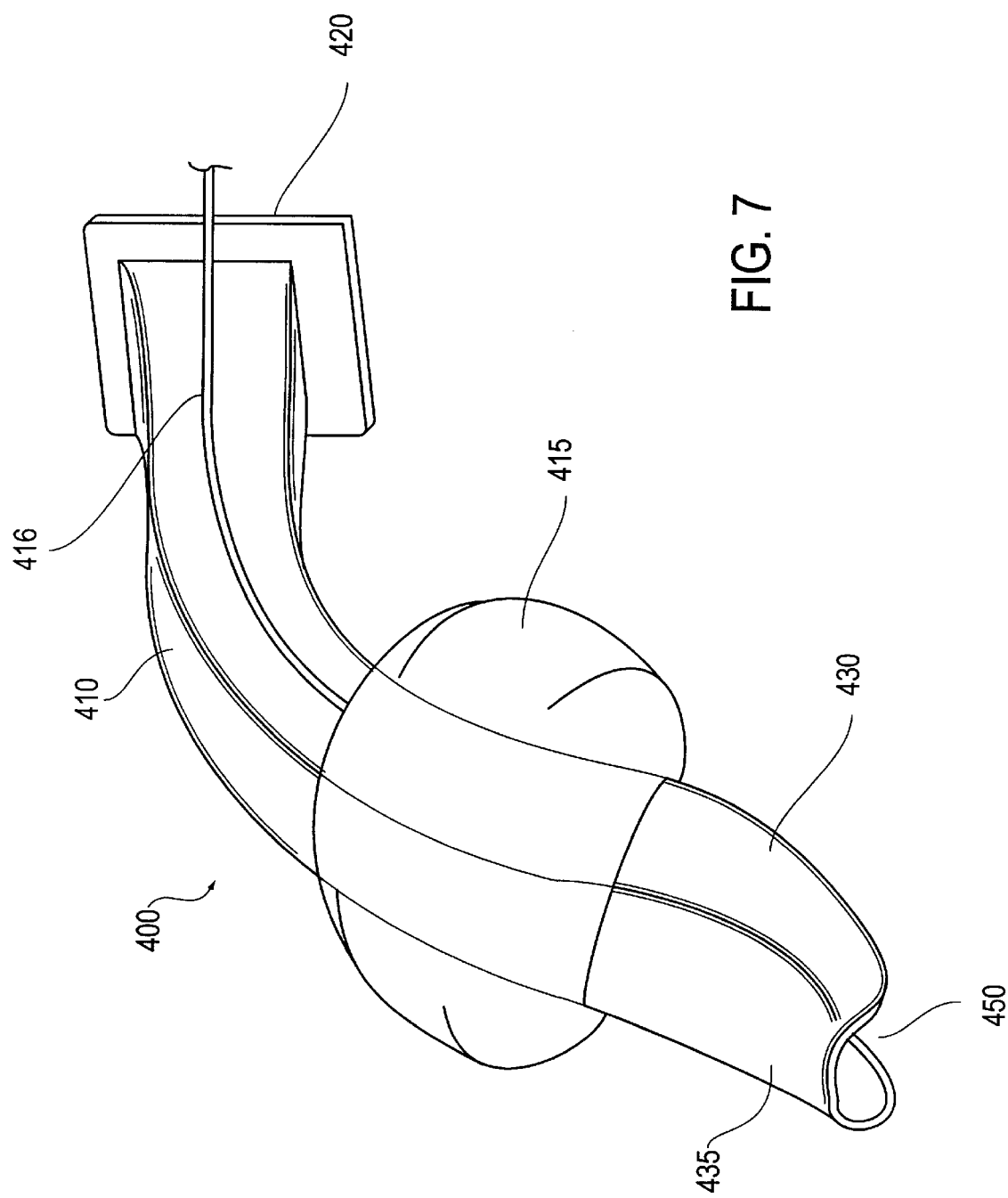
FIG. 7 shows a cuffed embodiment of the perilaryngeal oral airway according to the present invention.

FIG. 7 shows yet a further embodiment which includes an inflatable cuff 415 placed just above the distally positioned anterior notch 450. Again, like elements are denoted with like reference numerals, but preceded with the number "4". The cuff 415 is designed to be inflatable using a pilot tube 416 which includes a self-sealing proximal valve (not shown).

Upon inflation, the more distally positioned inflated cuff of the present invention is located within the hypo-pharynx and thereby allows the perilaryngeal oral airway of the present invention to be held in place without external means and avoids the airway leakage which can occur at the base of the tonsillar pillars and soft palate when using the conventional cuffed oro-pharyngeal airway.

Figure 8:
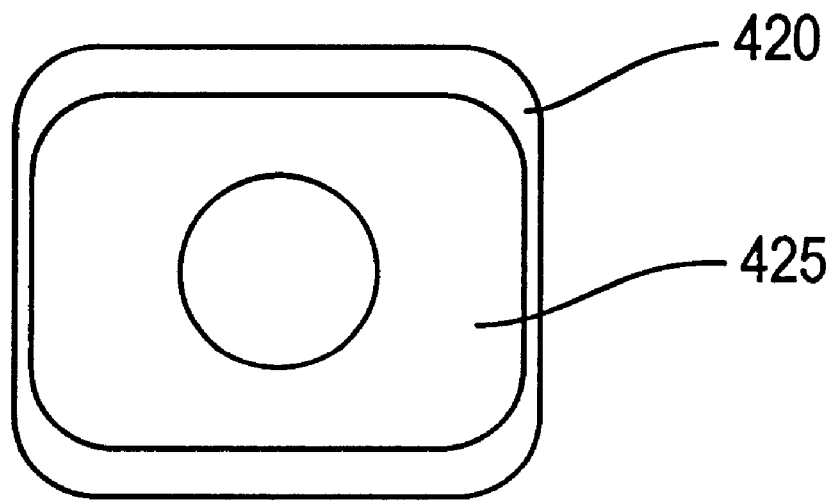
FIG. 8 shows a proximal end of the perilaryngeal oral airway of FIG. 7.

As shown in FIG. 8, in order to allow the cuffed airway 400 to be attached to an anesthesia circuit or other airway circuit, an adapter 425 is inserted into the flanged proximal end portion 420 of the oral airway. In the embodiment of FIGS. 7 and 8, the adapter 425 is placed inside the flanged proximal end portion 420 of the oral airway 400 and held in by means of friction. However, many other mechanisms (e.g., Luer-lock, notched, snap, etc.) may be utilized to retain the adapter 425 in the proximal end 420 of the oral airway. Alternatively, the adapter may be made so as to fit over the end of the perilaryngeal oral airway and still accomplish the desired purpose. Of course, the proximal end piece for permitting attachment to an anesthesia circuit or other airway circuit may be molded-in to the oral airway itself.

With respect to all of the above-discussed embodiments, the actual lumen or hollow portion of the perilaryngeal oral airway of the present invention may be dome-shaped (convex) at the posterior wall of the body member at least through the portion which is operative to be positioned within the patient's mouth in order to better approximate the anatomy of the oral passageway.

Moreover, as an alternative, the oral airway may terminate in the hypo-pharnx (below the base of the tongue) but still end above the epiglottis, so that it would function to hold soft tissues away from the air passageway. A further embodiment of this particular alternative might have both the anterior and posterior notch absent since it could terminate just above the epiglottis.

Although the preferred embodiments of the present invention have been described above by way of example, it would be understood by those skilled in the field that numerous modifications may be made to the disclosed embodiments without departing from the spirit and scope of the invention, which is defined by the appended claims.

What is claimed is:

1. An oral airway, comprising:
a curved hollow, tubular longitudinally extending body member which defines a patient airway passage therethrough for active ventilation of the patient's lungs by a practitioner, said body member having a distal end portion for insertion into the mouth and pharynx of the patient and a proximal end portion which terminates for location at the mouth of the patient and which is configured to be used together with at least one of a face mask, an anesthesia circuit, and a breathing circuit,
wherein said distal end portion of said body member is extended and shaped so as to be operative to scat deep in the patient's hypo-pharynx and surround the patient's epiglottis and glottis, thereby to hold the patient's soft tissue away from the patient's air channel opening.

2. The oral airway as claimed in claim 1, wherein said extended distal end portion of said body member is divided so as to form a pair of elongated extension walls which are operative to seat deep in the patient's hypo-pharynx and surround the patient's epiglottis and glottis, thereby to hold the patient's soft tissue away from the patient's air channel opening.

3. The oral airway as claimed in claim 1, wherein said extended distal end portion of said body member comprises a distal anterior wall having a notched portion, and a filled-in distal posterior wall which serves to hold the patient's tissue away from the patient's larynx.

4. The oral airway as claimed in claim 1, further comprising an inflatable cuff positioned just above said distal end portion of said body member.

5. The oral airway as claimed in claim 3, further comprising an inflatable cuff positioned just above said notched portion of said distal anterior wall.

6. The oral airway as claimed in claim 1, further comprising at least one air hole which passes through a posterior wall of said body member.

7. The oral airway as claimed in claim 1, further comprising at least one air hole which passes through a distal anterior wall of said body member.

8. The oral airway as claimed in claim 2, further comprising holes which pass through an anterior surface of said elongated extension walls.

9. The oral airway as claimed in claim 1, wherein said body member is of sufficient softness and pliability to bend during insertion into the patient and to accommodate different angles once inserted and seated in the patient.

10. The oral airway as claimed in claim 2, wherein the elongated extension walls are flexible and soft so that there is at least some give as the oral airway is inserted into the patient.

11. An oral airway, comprising:
a curved hollow, tubular longitudinally extending body member which defines a patient airway passage therethrough for active ventilation of the patient's lungs by a practitioner, said body member having a distal end portion for insertion into the mouth and pharynx of the patient and a proximal end portion which terminates for location at the mouth of the patient and which is configured to be used together with at least one of a face mask, an anesthesia circuit, and a breathing circuit,
wherein said distal end portion of said body member is divided so as to form a pair of elongated extension walls which are operative to seat deep in the patient's hypo-pharynx and surround the patient's epiglottis and glottis, thereby to hold the patient's soft tissue away from the patient's air channel opening.

12. An oral airway, comprising:
a curved hollow, tubular longitudinally extending body member which defines a patient airway passage therethrough for active ventilation of the patient's lungs by a practitioner, said body member having a distal end portion for insertion into the mouth and pharynx of the patient and a proximal end portion which terminates for location at the mouth of the patient and which is configured to be used together with at least one of a face mask, an anesthesia circuit, and a breathing circuit,
wherein said distal end portion of said body member comprises means for seating deep in the patient's hypo-pharynx and surrounding the patient's epiglottis and glottis, thereby to hold the patient's soft tissue away from the patient's air channel opening.

13. An oral airway, comprising:
a curved hollow, tubular longitudinally extending body member which defines a patient airway passage therethrough for active ventilation of the patient's lungs by a practitioner, said body member having a distal end portion for insertion into the mouth and pharynx of the patient and a proximal end portion which terminates for location at the mouth of the patient and which is configured to be used together with at least one of a face mask, an anesthesia circuit, and a breathing circuit,
wherein said distal end portion of said body member is extended and shaped so as to be operative to seat deep in the patient's hypo-pharynx and terminate just above the patient's epiglottis and glottis, thereby to hold the patient's soft tissue away from the patient's air channel opening.

14. A method of administering at least one of anesthesia and respiratory treatment to a patient, comprising:

providing an oral airway comprising a curved hollow, tubular longitudinally extending body member which defines a patient airway passage therethrough for active ventilation of the patient's lungs by a practitioner, said body member having a distal end portion for insertion into the mouth and pharynx of the patient and a proximal end portion which terminates for location at the mouth of the patient and which is configured to be used together with at least one of an anesthesia circuit and an airway circuit, wherein said distal end portion of said body member is extended and shaped so as to be operative to seat deep in the patient's hypo-pharynx and surrounding the patient's epiglottis and glottis, thereby to hold the patient's soft tissue away from the patient's air channel opening;

inserting the distal end portion of the oral airway into the patient's mouth and pharynx so that the distal end portion of the body member is seated deep in the patient's hypo-pharynx and surrounds the patient's epiglottis and glottis;

holding the patient's soft tissue away from the patient's air channel opening using the distal end portion of the oral airway; and attaching one of the anesthesia circuit and the airway circuit to the proximal end portion of the oral airway.

* * * * *